United States Patent [19]

Brooks et al.

[11] 4,448,200
[45] May 15, 1984

[54] SYSTEM AND METHOD FOR DYNAMIC BACKGROUND SUBTRACTION

[75] Inventors: Samuel H. Brooks, Los Angeles; Donald W. Crawford, Long Beach; Robert H. Selzer, Los Angeles; David H. Blankenhorn, Pasadena, all of Calif.

[73] Assignee: University of Southern California, Los Angeles, Calif.

[21] Appl. No.: 258,132

[22] Filed: Apr. 27, 1981

Related U.S. Application Data

[63] Continuation-in-part of Ser. No. 890,103, Mar. 27, 1978, Pat. No. 4,263,916.

[51] Int. Cl.³ .............................................. A61B 6/00
[52] U.S. Cl. .................................... 128/653; 128/660; 378/20; 378/151
[58] Field of Search ........................ 128/653, 660–663; 378/20, 151; 364/414; 358/111–112

[56] References Cited

U.S. PATENT DOCUMENTS 4,329,590  5/1982  Adelmeyer ........................... 378/151
4,335,427  6/1982  Hunt et al. ........................... 364/414

OTHER PUBLICATIONS

Brenneche, R. et al., "A Special Purpose Processor for Digital Angio-Cardiography Design & Applns.", Conf. Computers in Cardiology, Geneva, Switz., Sep. 26–28, 1979.

Brace, J. A. et al., "Computer-Controlled Cobalt Unit for Radio-Therapy", MBE, vol. 19, No. 5, Sep. 1981, pp. 612–616.

Primary Examiner—Kyle L. Howell
Assistant Examiner—Francis J. Jaworski
Attorney, Agent, or Firm—Nilsson, Robbins, Dalgarn, Berliner, Carson & Wurst

[57] ABSTRACT

An image acquisition system and method for generating a subtracted image motion picture as an imaging device moves relative to a subject includes an imaging device for first generating a sequence of first image frames as the imaging device moves along an imaging path under operator control and later generating a sequence of second image frames as the imaging device automatically moves along the same imaging path under processor control. Motion along the imaging path can be duplicated by sensing and storing information indicative of the position of the imaging device relative to the subject as a function of time and later commanding servo motors connected to the imaging device using that position information. Each frame in the first and second sequence of frames has position information stored therewith identifying the location along the imaging path at which each frame was generated. The first and second sequence of frames may then be aligned using the position information and subtracted on a frame-by-frame basis to obtain a subtraction image motion picture essentially free of background interference to detect change over time. The first and second motion pictures may be made at different points of time under similar circumstances either with or without the use of a contrast medium, and subtracted to obtain a difference picture to highlight changes over time.

31 Claims, 3 Drawing Figures

SYSTEM AND METHOD FOR DYNAMIC BACKGROUND SUBTRACTION

This application is a continuation-in-part application of co-pending application Ser. No. 890,103, filed Mar. 27, 1978 now issued as U.S. Pat. No. 4,263,916.

FIELD OF THE INVENTION

The present invention relates to image acquisition systems in the medical field and in particular to an image acquistion system for obtaining a substrated image motion picture of a subject wherein an imaging device which generates the image of the subject moves relative to the subject during image generation and storage.

BACKGROUND OF THE INVENTION

Image acquisition systems for visualization of various body organs and systems such as the cardiovascular system have won wide acceptance. For example, coronary cine or video angiograms are generated to discern the morphology and function of the coronary arterial vessels. However, other structures such as ribs and vertebra (background) diminish the ability to view the coronary arterial vessels. Consequently, various methods have been devised to decrease the background and enhance the areas of interest. For example, photographic or digital subtraction has been used to minimize or eliminate background. Background subtraction, as conventionally practiced, generally requires that two images be generated and recorded. The first image is usually generated without highlighting the vessels of interest with a contrast medium. The resultant picture or film is called a scout film. The second image is then generated and a second film obtained after the contrast medium has been injected into the vascular system so that the arterial vessels are highlighted. Common features of the first and second films are eliminated by subtracting the first film image from the second film image using well-known video (electronic), optical (photographic) or digital subtraction techniques.

In order to effect such subtraction, it is generally necessary to make two adjustments. The first adjustment is the registration of the first and second films by which corresponding elements of the two films are put into congruence. This is most simply done by translation and rotation of one of the images relative to the other. If there is any appreciable movement of the body between the two images, a more complex intraimage transformation may be required.

The second adjustment is the transformation of image density values into units of exposure. This is desirable so that the subtracted image will faithfully represent the vessel whether the background is dark or light.

Of course, the above techniques are useful in any of a number of different types of image acquisition systems such as cine, video, cut film, CAT, scan or ultrasound image acquisition systems.

Heretofore video, optical or digital subtraction techniques required that the image generator, such as the camera for a cine system or the image intensifier for a television or video system, and the subject remain stationary relative to each other during the entire time that the first and second films or digitized picture were generated. Indeed, one of the problems which has existed in prior subtraction techniques has been the necessity of assuring that the subject remains perfectly stationary and immobile during the entire time that the images are generated and stored. Even slight relative movement between the imaging device and the subject creates misregistration between the first film and the second film, thus resulting in blurring and a consequent lack of definition in the resultant subtracted image film.

This has also prevented extensive use of subtraction techniques in angiography because it has been general angiographic practice to pan the camera or other imaging device during the injection of the contrast medium. By this means, the flow of the contrast medium can be observed through the arterial bed without sacrificing details. When it is desired to use this panning process substantial amounts of contrast medium must be injected into the subject to get the desired degree of definition of the arteries without an unacceptacle level of background interference. This can be dangerous to the subject.

A procedure recently adopted to alleviate the danger of high contrast medium concentrations has been to take a number of pictures of a subject with a decreased amount of contrast medium and thereafter register and average the multiple pictures to provide the degree of definition desired. Such a technique was the subject of our patent application entitled "Image Averaging for Angiography by Registration in Combination with Serial Images," U.S. Pat. No. 4,263,916, of which this application is a continuation-in-part. This technique is very useful but was particularly directed to multiple pictures of the subject at a fixed position relative to the imaging device. Such is not the case when the imaging device pans the subject.

Of course, various other techniques are known for combining multiple images to form a composite image. However, such techniques have not been heretofore used in conjunction with image subtraction where there is relative movement between the imaging device and the subject during a panning procedure.

The present invention provides for such subtraction even though there is relative movement between the imaging device and the subject by providing apparatus whereby the motion between the imaging device and the subject can be sensed, stored and later duplicated so that frame-by-frame background subtraction can be done. The present invention is applicable in the fields of radiography, angiography, digital angiography, ultrasound scanning, nuclear imaging, CAT scanning or any other type of imaging.

More specifically, the present invention comprises apparatus and methods for sensing and recording relative position parameters between the imaging device and the subject over a period of time to describe completely the motion geometry between the imaging device and the subject along a movement path selected by the operator. The positional parameters are then used to generate commands which drive a servo motor system whereby all or part of the imaging device is moved to duplicate the operator's original movement path. Reference to the imaging device herein includes the support table for the subject, an illumination source and an illumination receiver and movement of the imaging device means movement of one or more components of the imaging device to effect relative movement between the subject and the illumination receiver.

In accordance with the invention, a first sequence of images is recorded to define a first motion picture as movement occurs along the movement path under operator control and a second sequence of images is recorded to define a second motion picture as subsequent movement occurs along the movement path under automatic control.

The first and second motion pictures may be made immediately after each other in which case the first motion picture is made while a contrast medium is in the arterial bed of the subject and the second motion picture is made after the contrast medium has been substantially diluted or otherwise purged from the arterial bed.

Alternatively, the first and second motion pictures may be made with a substantial time interval of even several years therebetween so that the subtracted image motion picture will be a difference motion picture highlighting the changes which occurred during the time interval between the first and second motion pictures. With respect to this latter case, if a contrast medium is to be used, as is generally desired in radiographic imaging, then both the first and second motion pictures should be generated while the contrast medium is in the arterial bed. Otherwise, neither the first nor the second motion picture should be made while there is contrast medium in the arterial bed.

The individual frames of both the first and second motion pictures, whether or not taken with a contrast medium present are then associated with a particular position along the movement path so that every first motion picture frame is associated with a corresponding second motion picture frame by aligning the frames according to correspondence of the associated position information. While there would necessarily be some non-congruence due, for example, to subject respiration, movement and cardiac cycle, by techniques such as timing or multiple or very slow second motion picture runs, it is possible to get or select second motion picture frames which are in good registration with the first motion picture frames. Translation, rotation and more complex transformations may also be used in accordance with the invention to insure satisfactory infraframe registration. Similarly, recording or image intensifier information and step wedge information enables suitable nonlinear subtraction to be carried out.

SUMMARY OF THE INVENTION

The present invention comprises an image acquisition system for obtaining a subtracted variable density motion picture of selected features of a subject where there is relative movement between the subject and a receiving means while the motion picture is being taken. The system in accordance with the invention includes a source of illuminating energy such as an X-ray tube, an ultrasonic source or other suitable means for illuminating the selected feature of the subject and a means for receiving the illuminating energy and generating a variable density image therefrom.

A support for the subject is positioned between the illuminating energy source and the receiving means. Means are provided for selectively changing the relative position between the support and receiving means to define a first relative movement path therebetween with position sensing means interconnected for sensing the relative position between the support and the receiving means as the receiving means and support move relative to one another. The position sensing means generates position signals representative of the relative position along the first relative movement path. Means are provided for thereafter storing the sensed position signals and subsequently generating position control signals from these stored position signals.

The position control signals are provided to a means for driving either the support or the receiving means to vary the relative position between the support and the receiving means in response to the position control signals to thereby define a second relative movement path which is substantially duplicative of the first relative movement path.

Means are also included for generating a first motion picture of the variable density image of the selected feature of the subject during the relative movement along the first relative movement path and generating a second motion picture of the variable density image of the selected feature of the subject during the relative movement along the substantially duplicative second relative movement path. The first motion picture is defined by a plurality of first frames where each first frame defines a picture taken at a specific geometric position along the first relative movement path. Similarly, the second motion picture has a plurality of second frames where each second frame defines a picture taken at a specific geometric position along the second relative movement path. Means for aligning the first frames in the first motion picture with the second frames in the second motion picture are provided whereby each aligned first frame and second frame represent variable density images at substantially corresponding geometric positions relative to the subject along the respective first and second relative movement paths. Finally, means are provided for subtracting each second frame taken along the second path from each corresponding aligned first frame taken along the first path for defining a plurality of subtracted variable density frames to define the subtracted variable density motion picture.

BRIEF DESCRIPTION OF THE DRAWINGS

A complete understanding of the present invention and of the above and other advantages thereof may be gained from a consideration of the following description of the preferred embodiments taken in conjunction with the accompanying drawings in which.

DETAILED DESCRIPTION

Figure 1:
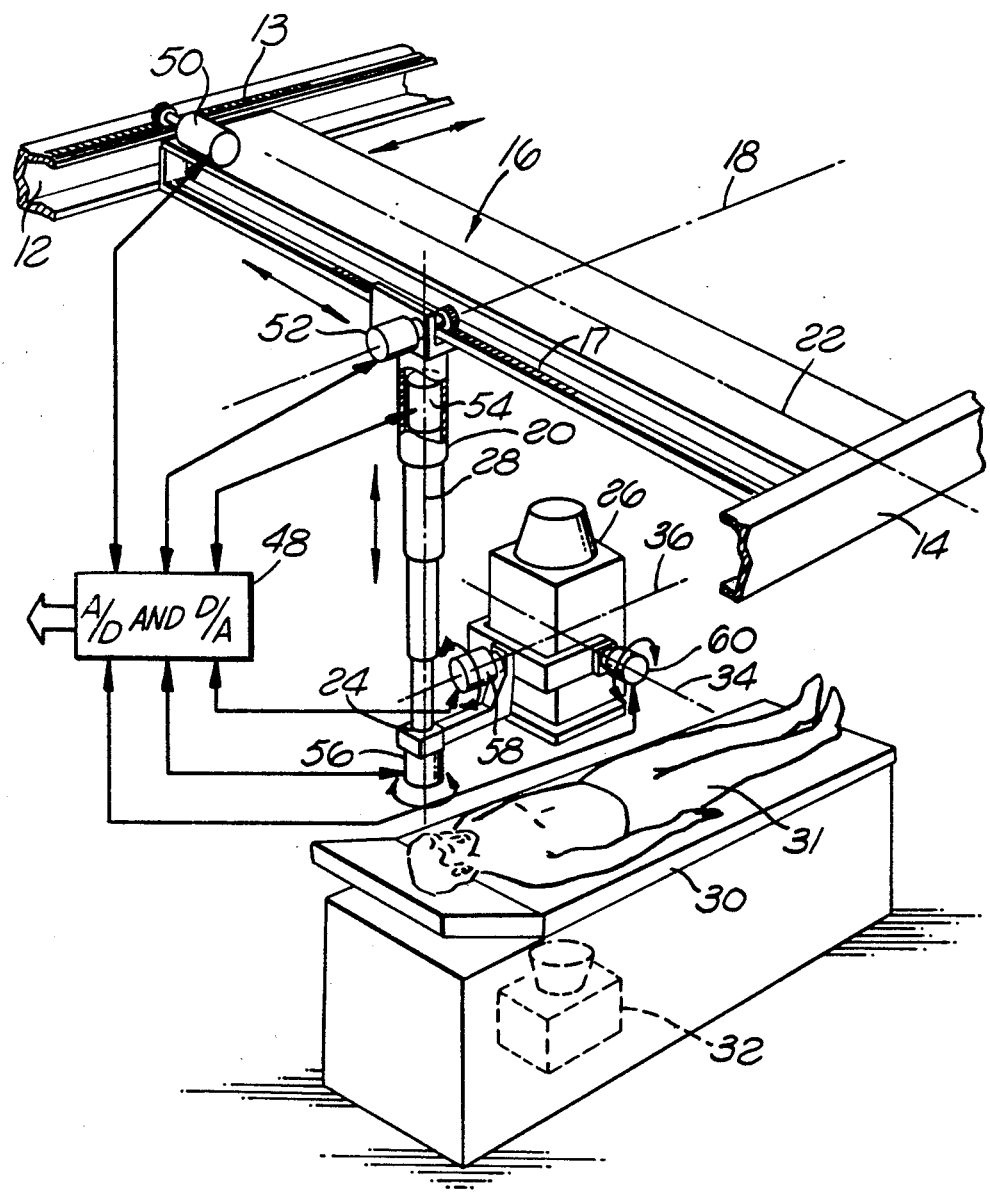
FIG. 1 is a simplified representation of a system incorporating a plurality of servo motors and sensors to sense the relative motion between an imaging device and a support table and enable subsequent repetition of that relative motion.

The present invention encompasses an image acquisition system and method for generating a first motion picture as relative motion occurs between an imaging device, which includes an illumination source, a support table for the subject and an illumination receiver, and a subject and automatically controlling either or both of the illumination receiver and support table to duplicate the movement path at a later time while the imaging device is generating a second motion picture. The frames of the first and second motion pictures are then aligned and registered and then subtracted to obtain a subtracted image motion picture where only the differences between the first motion picture and the second motion picture are visible.

The resultant subtracted image motion picture can be used in a number of ways. For example, the apparatus and method is useful in angiography where a contrast medium is injected into a subject and the first motion picture made while the contrast medium is in the arterial bed of the patient or subject. The first motion picture can therefore be made as, for example, the imaging means pans a stationary subject wherein only dilute solutions of contrast medium are used. The second motion picture is then generated along the same movement path as soon as the contrast medium has become sufficiently diluted or has otherwise been purged from the arterial bed of the subject. Generally the second motion picture can be made within several minutes after the first motion picture has been made. The resultant subtracted image motion picture is then a motion picture of the arterial bed highlighted by the contrast medium flowing therethrough. The subtraction process substantially eliminates the density variations due to background images of the bone and tissue.

The present invention can also be used to generate a subtracted image motion picture which highlights the differences in the subject's physiology which have occurred over time such as the degeneration or healing of particular organs of the subject. Such a subtracted image motion picture showing differences can be made by first positioning a subject on a support table and thereafter generating the first motion picture as the operator moves the illumination receiver, support table or both along an operator selected first movement path. The first motion picture may be generated with or without a contrast medium present in the arterial bed of the subject.

At a later time, hours, weeks, or even years later, the subject is again positioned on the support table at a position as nearly identical as is possible to that which existed when the first motion picture was taken. The original operator's selected movement path is then automatically duplicated under computer control by commanding movement of the illumination receiver, support table or both to duplicate the movement previously selected by the operator. If the first motion picture was generated with a contrast medium in the arterial bed, then the second motion picture should preferably also contain the contrast medium in the arterial bed of the subject. In general a contrast medium will be utilized when the imaging acquisition system is radiographic. However, contrast medium is not used when the imaging device is an ultrasonic system. Of course, it will be appreciated that even with radiographic image acquisition systems a contrast medium is not absolutely necessary to generate a subtracted motion picture indicative of the differences in certain organs of a subject which have occurred over an interval of time.

Specific apparatus for effecting relative movement between the imaging device and the subject are well known. For example, the bilateral suspension system produced by General Electric Medical Systems Department provides an apparatus whereby a fluorocon (illumination receiver) can be positioned along three orthogonal translational axes. Once the fluorocon is so positioned, the support table moves with the fluorocon remaining stationary.

Other systems permit the illumination receiver to move along up to three orthogonal translational axes or up to three orthogonal rotational axes. In such systems, the support table remains stationary while the illumination receiver moves relative to the support table and subject. It is therefore possible, utilizing such systems, for the operator to move the illumination receiver in one or more of up to six different degrees of freedom.

In addition to moving the support table, the illumination receiver or both to define the movement path, it is also possible to move the source of illuminating energy. Generally, the source of illuminating energy is positioned on one side of the subject and the illumination receiver is positioned on the other side of the subject. It may be necessary to move the illuminating energy source as the illumination receiver, for example, moves so that the illumination receiver will not move out of the field of energy emanating from the illuminating energy source.

Although any one of a number of different mechanisms can be incorporated to provide for translational or rotational motion of either the illumination receiver or the support table and suitable position changes of the illuminating energy source as required, the system to be described hereafter and illustrated in FIG. 1 provides for a stationary support table and a movable illumination receiver where movement is permitted about one or more of three orthogonal translational axes and three orthogonal rotational axes. It will be appreciated, however, that in accordance with the invention any other movement mechanism is possible and the system illustrated in FIG. 1 is to be taken as being only illustrative of the invention.

Therefore, referring to FIG. 1, one possible six degree of freedom system 10 which may be used in accordance with the invention incorporates a pair of elevated spaced-apart stationary rails 12 and 14 with a beam 16 movably mounted on the rails 12 and 14 to provide translational movement along an axis 18 parallel to the rails 12 and 14. A telescopic column 20, having an end 24 remote from the beam 16, is movably attached to the beam 16 by any suitable means to provide translational movement along an axis 22 parallel to the beam 16 and orthogonal to the axis 18. The telescopic column 20 has a remote end 24 to which the illumination receiver 26 is rotatably attached. The telescopic column moves vertically up and down along an axis 28 which is orthogonal to both axes 18 and 22.

The illumination receiver 26 is mounted to the end 24 of the telescopic column 20 to be rotatable about one or more of up to three orthogonal axes. For example, the illumination receiver 26 may be attached to the telescopic column 20 to be rotated about the vertical axis 28; to be tilted about a tilt axis 34 which is perpendicular to the vertical rotation axis 28; and pivoted about a pivot axis 36 which is perpendicular to both the vertical rotation axis 28 and the tilt axis 34.

The particular interconnection and support mechanisms by which the illumination receiver can be rotatably mounted to rotate, tilt and pivot about orthogonal rotation axes are well known and will not be specifically described herein. Of course, it will be appreciated that many other possible mechanical linkages are possible within the scope of the present invention to provide for translation motion along one or more orthogonal axes or rotational motion about one or more rotational axes to effect relative movement between the illumination receiver and the subject 31 on the table 30.

While mechanical apparatus are available which enable an operator to selectively move either the support table 30 or the illumination receiver 26 in any of up to six degrees of freedom, it has not been heretofore known to generate a first motion picture as the position of the illumination receiver 26 is moved along a first path relative to the subject 31 and thereafter to retrace that movement path to generate a second motion picture which can be aligned and registered and thereafter subtracted from the first motion picture on a frame-by-frame basis to achieve a substracted image motion picture of a subject while there is relative motion between the subject 31 and the illumination receiver 26.

Therefore, in accordance with the invention, apparatus illustrated in FIG. 1 includes a plurality of position sensing devices whereby the translational position of the illumination receiver along each translational axis 18, 22 and 28 and the angular position about each of the rotational axes 28, 34 and 36 during the movement of the illiumination receiver by an operator is sensed. In one embodiment, the sensors may be suitable servo motorswhich are well known in the field of servo systems. It is well known that servo motors can serve as either a signal generator or a motor depending on whether the servo is caused to rotate in response to an external mechanical force or in response to an electrical signal respectively. Thus, by suitably connecting servo motors to detect or cause translational and rotational movement along or about each of the translational and rotational movement axes, it is possible to generate a position signal for each which varies with time and is indicative of the movement path along each axis. By digitizing and storing each of these signals and then later using the stored signals to command the servos, it is possible to duplicate substantially the original movement path selected by the operator.

Thus, referring again to FIG. 1, a suitable rail servo motor 50 may be fixed to the movable beam 16 and positioned to engage the stationary rail 12 so that as the movable beam 16 moves along the stationary rail, the rail servo 50 will rotate thereby generating a signal indicative of the position of the movable beam 16 relative to the stationary rail 12. Such a mechanical interrelationship may be provided by suitable linear gear teeth 13 along the rail 12 or any other suitable means.

Alternatively, a position signal may be generated indirectly by a suitable sensor. One such indirect sensor may be provided by a resistive strip positioned along the entire length of one of the stationary rails where the resistive strip has a resistance gradient along its length. A pressure applying flange could then be fixed to the movable beam and positioned to press against the resistive strip and complete a circuit. As the beam 16 is moved, the position at which pressure is applied would change and the resistance would also change. The variation in voltage across the resistor strip would thus be indicative of the position of the movable beam 16 relative to the stationary rails 12 and 14. Of course, any other suitable mechanism could be provided whereby a signal was generated either directly or indirectly by analog or digital means to indicate the position of the movable beam 16 along the stationary rails 12 and 14.

In a similar manner, a beam servo 52 fixed to the telescopic column 20 may be provided to engage a gear 17 or other mechanism along the movable beam 16 to generate an electronic signal indicative of the position of the telescopic column 20 along the movable beam axis 22.

Likewise, a column servo 54 could be fixed to the telescopic column 20 for generating an electronic signal representative of the vertical position of the telescopic column 20 along the vertical axis 28 at each point in time thereby indicating the vertical height of the illumination receiver.

In a similar fashion, a rotation servo motor 56, a tilt servo motor 58 and a pivot servo motor 60 may be suitably and conventionally mounted to generate signals indicative of the angular position of the illumination receiver 26 about the rotation axis 28, the tilt axis 34 and the pivot axis 36, respectively.

The resultant time varying analog position signals from the servo motors 50, 52, 54, 56, 58 and 60 are interconnected to suitable analog-to-digital converters 48 which digitize each of the analog position signals. Each digitized position signal comprises a series of numbers representative of the position of the illumination receiver along a particular movement axis at a particular instant of time.

In operation, an operator simply grasps and manually moves the illumination receiver, 26 along a desired movement path relative to the subject 31. As the illumination receiver 26 moves, each of the above-described servo motors generate analog or digital signals indicative of the position of the illumination receiver along each of the three orthogonal translational axes and about each of the three orthogonal rotational axes. In accordance with the invention, the position signals, whether analog or digital, are then stored in a suitable memory such as a computer memory.

While the operator is moving the illumination receiver relative to the subject 31 thereby generating the position signals, the illumination receiver is generating and storing a sequence of image frames to define a first motion picture. Each frame of the first motion picture is stored utilizing a suitable memory such as a computer core, disc, tape cassette memory or a photographic memory medium such as photographic film. As previously described, the second motion picture is then generated by the illumination receiver as the system retraces and substantially duplicates the first movement path.

It is, of course, desired that the subject be in substantially the same position on the support table when the first and second motion picture are generated. Such would generally be the case where the first motion picture and the second motion picture are made within several minutes according to the method previously described where the first motion picture is taken with a constant medium in the arterial bed of the subject and the second motion picture is taken after the contrast medium has either become sufficiently dilute or has been purged from the arterial bed of the subject.

On the other hand, in the second situation previously described where the time interval between the generation of the first motion picture and the generation of the second motion picture is several hours, weeks or even years so that the differences by way of either healing or deterioration of body organs is shown, it is necessary to position the subject in substantially the same position during the generation of the second motion picture as existed when the first motion picture was generated. However, in accordance with one aspect of the invention, the subject need not be placed in exactly the same position on the table so long as the approximate position is substantially the same. Specifically, in accordance with a registration method which may be used in conjunction with the present invention, it is possible to shift each frame up and down and right and left and to, in effect, twist each frame a small amount to achieve registration between the two corresponding but slightly misregistered motion picture frames of the first and second motion pictures respectively. Consequently, it is not essential, as in prior subtraction systems, to position the subject in exaclty the same location on the support table to achieve registration of the images. The specific means for achieving such frame-to-frame registration between the first and second motion pictures will be described in greater detail hereafter.

Referring again to FIG. 1, the previously stored position data is outputted from the computer memory and is converted back to a time varying analog signal in the digital-to analog converter 48 wherein the analog position signals are interconnected to drive the rail servo motor 50, the beam servo motor 52, the column servo motor 54, the rotation servo 56, the tilt servo 58, and the pivot servo 60 respectively, to cause the illumination receiver to duplicate the movement path originally followed by the operator. The second motion picture is then generated and stored as the illumination receiver retaces the original movement path selected by the operator in the same manner as when the first motion picture was generated.

Figure 2:
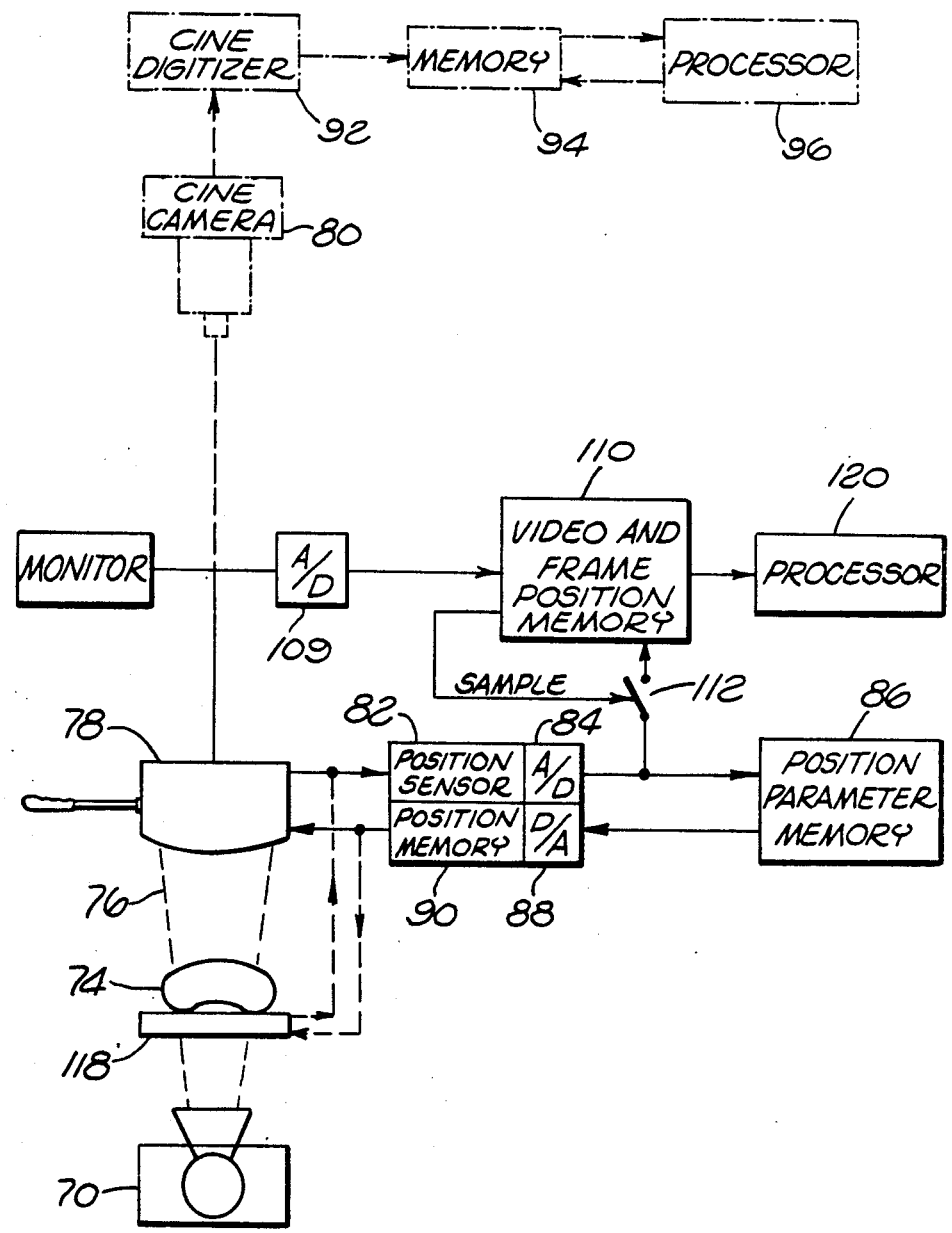
FIG. 2 is a block diagram of a representative system incorporating a cinegraphic camera.

Referring now to FIG. 2, a radiographic system in accordance with the invention may include, for example, an illumination source such as an X-ray tube 70 for providing a source of X-rays, a support table 72 for supporting a subject 74 in a beam of X-ray 76, and an illumination receiver 78 such as a fluorocon positioned above the subject 74 to receive the X-rays 76 passing through the subject 74. The illumination source, support table and illumination receiver together comprise the imaging device. In such an arrangement, the X-rays passing through the subject are variably attenuated depending on the local density of the subject to produce a variable density image of the subject which is received by the illumination receiver 78. A suitable recording device such as a cine camera 80 or a video digitizer 109 and memory 110 generates the first motion picture as the illumination receiver and/or support table are moved by the operator along the movement path.

As movement occurs along the first movement path, servos or suitable indirect position sensors 82 generate a plurality of position signals indicative of the geometric position of the illumination receiver 78 relative to the support table 72 and hence the subject 74. Each of the position signals is then digitized in a digital-to-analog converter 84 to define digitized position signals which are stored in a position parameter memory 86. Subsequently, the digitized position information stored in the position parameter memory 86 is sequentially outputted in the same order that it was stored and is converted to a plurality of analog signals in the digital-to-analog converter 88. The resultant analog signals are each directed to one of the servo motors 90 to move the illumination receiver 78 and/or support table 72 along a path substantially the same as the first relative movement path.

As the illumination receiver 78 and/or support table 72 move in response to the servos 90 to duplicate the first relative movement path, the images are again recorded as before on the recording device to generate the second motion picture.

In the embodiment where cinegraphic motion pictures are generated, the first cinegraphic motion picture and the second cinegraphic motion picture may be optically aligned on a frame-by-frame basis. A photographic substraction process may then be performed on a frame-by-frame basis to generate a subtracted cinegraphic motion picutre. The particular theory and method of photographic subtraction is fully described in the article "Photographic Subtraction, I. Theory of Subtraction Image" by Hardstedt and Welander, *Acta Raciologica Diagnosis Vol.* 16 (1975); and "Photographic Subtraction, II. Technical Aspects and Method" by Hardstedt, Rundelius and Welander, *Acta Radiologica Diagnosis* 17 (1976) Fasc. 1 January, both of which articles are herein incorporated by reference.

Alternatively, the first cinegraphic motion picture and the second cinegraphic motion picture may be digitized on a frame-by-frame basis in cinegraphic digitizer 92 wherein each cinegraphic film is divided into an array of picture elements (pixels) where each pixel has a unique x,y coordinate address within the frame and each pixel has a numerical value representative of the illuminating energy density at that pixel coordinate address. Each digitized cinegraphic frame may then be stored in a memory 94 so that each frame of the first cinegraphic motion picture and each digitized frame of the second motion picture are stored in the memory 94.

The cinegraphic digitizer 94 may, for example, be simply a television video camera which is used to transfer the motion picture from a film medium to an electronic or video tube medium as the motion picture is being run. The video information can then be easily digitized in a conventional manner as described in "Computerized Fluoroscopy: Digital Subtraction for Intravenous Angiocardiography and Arteriography" by Crummy et al., December 1980, *AJR:*135, pp. 1131–1140, which article is herein incorporated by reference.

The digitized cinegraphic motion picture stored in memory 94 and the second cinegraphic motion picture stored in the memory 94 may then be aligned as described in our copending application Ser. No. 890,103 filed Mar. 3, 1978 which is herein incorporated by reference, so that each frame of the digitized first motion picture is aligned with the frame of the digitized second motion picture which was generated when the relative position between the imaging device 78 and the subject 74 along the movement path was the same as that at which the aligned first motion picture frame was generated. Such alignment may be done manually (visually) prior to the cinegraphic digitation so that the first frame of the first cinegraphic motion picture will correspond to the first frame of the digitized second cinegraphic motion picture. Each subsequent frame of the first cinegraphic motion picture and the second cinegraphic motion picture will then be likewise aligned provided the first and second motion picture were taken at the same film speed.

Although such alignment may be reasonably good, it is possible and indeed likely that the subject 74 will be in slightly different positions in the first and second motion pictures. Furthermore, it is likely that the individual aligned frames of the first and second motion pictures will have been generated at very slightly different geometric locations along the first relative movement path. Consequently, there is a need, once the above-described frame-to-frame alignment has been made, to provide a means of registering the images in each pair of aligned motion picture frames. Such registration of each second motion picture frame with each aligned first motion picture frame may be achieved using processor 96 by a suitable computer algorithum whereby subgroups of pixels in each of the second motion picture frames are sequentially shifted up or down until, for example, the sum of the difference between corresponding pixel density values of the subgroups is at a minimum. This subgroup registration is performed on a computer using the Fortran program entitled LANDMARK, a listing of which is appended hereto in Appendix A.

Because adjacent subgroups of pixels may overlap or become spaced apart after the above shifting process of individual pixel subgroups, a second computer program may be used to further shift individual pixel subgroups up or down or sideways to eliminate such gaps and overlaps. This procedure may likewise be accomplished on a computer using a Fortran program entitled TRANSFOR and a program entitled P1R, a listing of each of which is appended hereto in Appendix B. Utilizing such an approach, each frame in the second motion picture can be adjusted up and down, sideways, and can in effect be rotated or twisted to achieve optimal registration with the corresponding frame in the first motion picture.

Once registration of the two frames has been achieved through the above-identified pixel position adjustment procedure, the illumination energy density value of each pixel of each second motion picture frame is subtracted (either linearly or nonlinearly) from the illumination energy density value of the registered pixel of the corresponding first motion picture frame to generate a plurality of digitally subtracted frames which together define a digitally subtracted motion picture. The digital subtraction may likewise be done on a computer using a fortran subtraction program entitled SUBTRACX, a listing of which is appended wherein hereto as Appendix C. The digitally subtracted motion picture can be displayed on a television monitor or other suitable device in a conventional manner.

Of course, it will be appreciated that digital subtraction of still radiographic images is known and that such subtraction may be performed linearly or nonlinearly. More specifically, it has been known that images may be subtracted to produce a resultant image which presents the features of interest separated from features which are the same in each of two images. This may be done, for example, in angiography where a scout film of the background is first made followed by the making of another film after injection of a contrast medium in an artery. By subtracting the scout film from the contrast medium film, the background is removed leaving only the image of the artery with the contrast medium therein. Such subtraction may be done by analog techniques as with video systems or by digital techniques if the image is so represented.

If the densities of the images are well approximated by a linear function of the irradiation or other illuminating energy, then simple linear subtraction is adequate. This happens, for example, when the range of density is small. In general, however, the range of densities is large and nonlinear so that a more suitable technique must be employed to obtain a more satisfactory subtraction image.

Figure 3:
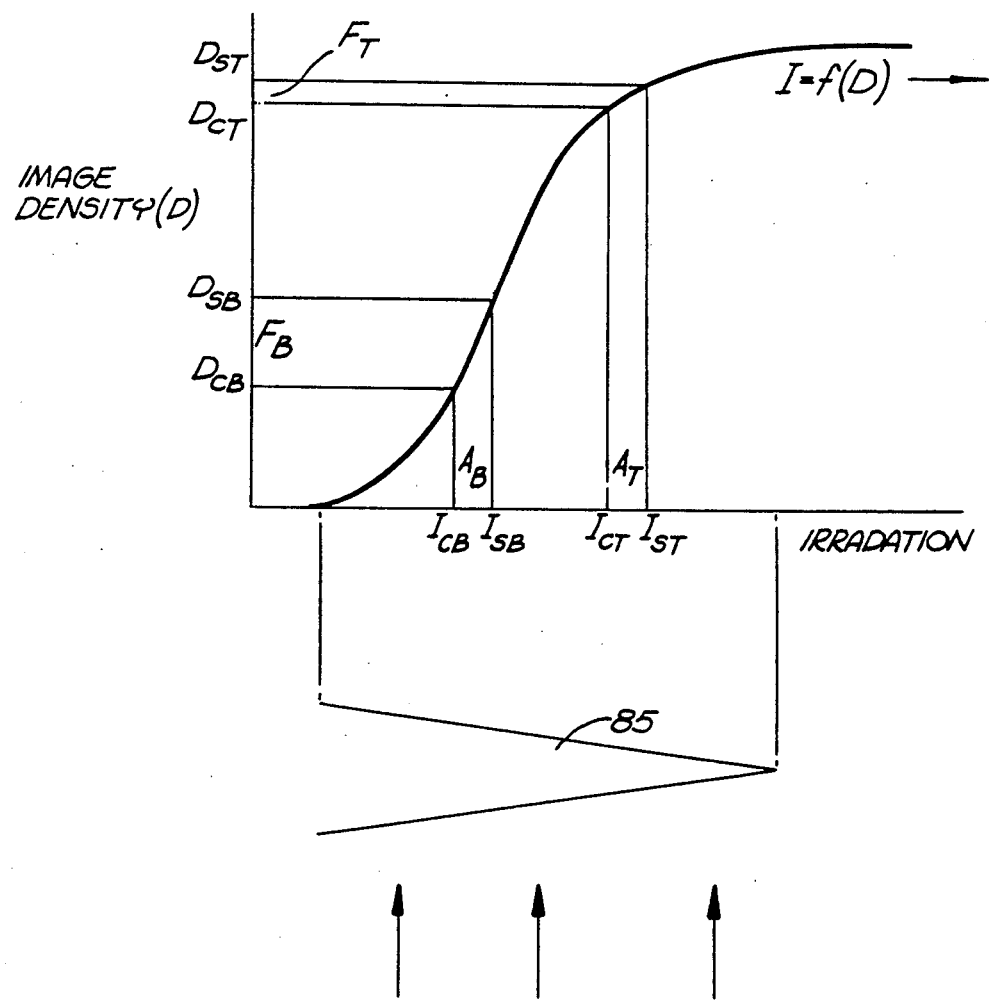
FIG. 3 is a characteristic curve of the image density plotted versus the light intensity.

More specifically, it is known that a chord length through a vessel is a function of the incident irradiation which is attenuated when the biological vessel is filled with contrast medium. Referring to FIG. 3, when there is no contrast medium present in the vessel and the background is uniform tissue, the incident radiation is attenuated to $I_{ST}$, where the ST signifies a scout film with the irradiation passing only through tissue. For the same cord through the same vessel under identical conditions, with the vessel filled with a uniform mix of contrast medium and blood, the attenuated irradiation is $I_{CT}$ where CT signifies a contrast medium through only tissue. If the contrast medium concentration is not too great, then the chord length is well approximated by the linear function $I_{ST} - I_{CT} = A_T$.

If the background is somewhat different, i.e., if it includes bone in the same ray that includes the vessel cord, then the chord length would again be approximated by the differential attenuation $I_{SB} - I_{CB} = A_B$, where the B means that there is bone as part of the background for both the scout and contrast medium films.

It is well known that film densities are a nonlinear function of the attenuated irradiation. As a result, the chord length which produced an attenuation differential of $A_T$ in tissue would produce a film density differential of $D_{ST} - D_{CT} = F_T$. An equivalent chord length in a background which includes bone would produce a film density differential of $D_{SB} - D_{CB} = F_B$. In general, $F_T$ does not equal $F_B$, as illustrated in FIG. 3.

Given the relation of density and irradiation it is possible to obtain the irradiation value I corresponding to any density value D, i.e., $I = f(D)$, so that the differential attenuation between the scout and contrast medium films results in an unbiased estimate of relative chord length. This relation can be empirically derived by use of a suitably constructed wedge X-rayed under the same conditions as at least one of the contrast medium or scout frames as illustrated by the wedge 85 in FIG. 3.

In order to obtain an irradiation attenuation A from a differential film density F, it is merely necessary to divide the film density differential F by the local derivative value of $I = f(D)$. As a result, a value is obtained which is proportionate to the chord length whatever the background.

For example, referring to FIG. 3, if the density D of the image is a nonlinear function of the irradiation I from the irradiating source, all density values across the image can be normalized so that, for example, a difference between the density between the one portion of the scout frame and a registered portion of the contrast medium frame where the background is tissue will be the same as the difference between a portion of the scout frame and a registered portion of the contrast medium frame where the background is bone. Such normalization can be achieved utilizing the curve shown in FIG. 3 by simply dividing $F_T$ which is the difference $D_{ST} - D_{CT}$ by the slope of the curve $I = f(D)$ at a point along the curve between $D_{ST}$ and $D_{CT}$. In general, the slope along the curve $I = f(D)$ between the point $D_{ST}$ and $D_{CT}$ will be approximately constant.

In the similar manner, the density value of the portion of the image through bone $D_{CB}$ is subtracted from the density of the registered portion of the scout film $D_{SB}$ yielding a difference $F_B$ which, when divided by the average slope or the slope at some point of the curve $I = f(D)$ between the points $D_{SB}$ and $D_{CB}$, will yield the same normalized density value. Such is the desired result, since the only difference in both cases is the fact that the irradiation passes through a different background.

Referring again to FIG. 2, the first and second motion pictures may be generated directly from the video signals generated by the illumination receiver 78 as when the illumination receiver 78 is a fluorocon. In such an embodiment the video signals generated by the illumination receiver 78 are digitized in an analog-to-digital converter 109 and then stored in a video frame and position memory 10. In order to be able to align each digitized first motion picture video frame with a corresponding digitized second motion picture frame, it is necessary to be above to identify the point along the relative movement path at which each frame was generated. One method of storing the geometric position data for each video frame is to generate a sample enable signal after each frame has been digitized and stored in the video and frame position memory 110. The sample enable signal then closes a switch 112 which causes the position data to be sampled and stored along with the video information in the video and frame position of memory 110. Thus, each frame of video information stored in the memory 110 has associated with it position information defining the position along the movement path at which the video frame was generated.

Subsequently, when the movement path is duplicated, video information is again generated and stored in a similar manner in the video and frame position memory 110. Position data is again sampled and stored at the end of the generation of each frame of the second motion picture.

The position data sample for the second motion picture frames may be taken by either sampling the digitized command information transferred from the position parameter memory 86 to the digital-to-analog converter 88 or alternatively, may be the digitized position data from the analog-to-digital converter 84 which is indicative of the actual position of the illumination receiver.

Once the sequence of video frames and the associated position of each frame has been generated along the first movement path for the first motion picture and the second motion picture, the frames of the first motion picture and the second motion picture may be processed in a processor 120 in a manner similar to that previously described.

More specifically, the various frames of the first motion picture can be aligned with the corresponding frames of the second motion picture by comparing the position data stored with each set of frame pixel data and aligning those frames having substantially the same stored position data, thus indicating that the frames were generated at the same relative position along the relative movement path.

It will, of course, be appreciated that the position data of the corresponding frames of the first motion picture and the second motion picture may not be precisely identical simply becuase it is unlikely that the sampling of the position data would have occurred at precisely the same points along the movement path for both the first and second motion pictures. Thus, the processor 120 may be utilized to round off or truncate the position data or to otherwise allow some variance in comparing the specific position data of the first and second motion picture frames to generate a positive comparison of position data so that corresponding frames of the first motion picture and the second motion picture can be aligned.

Once the individual frames of the first motion picture and the second motion picture have been aligned, the processor 120 can perform a suitable registration adjustment within one or both of the plurality of pairs of aligned frames as previously described and thereafter perform either linear or nonlinear subtraction as previously described.

It will also be appreciated that while previous reference has been made to registration between aligned frames of the first motion picture and the second motion picture, a composite first motion picture may be generated and used by first registering and then averaging several adjacent frames of motion picture information utilizing the registration routine attached hereto. Similarly, a composite second motion picture comprised of a plurality of sequential composite frames may be generated and used where each composite frame is generated by registering several adjacent frames of the first motion picture and then averaging those registered frames in accordance with the techniques previously described in conjunction with our Application Ser. No. 890,103 filed Mar. 27, 1978.

It will be appreciated of course that various other embodiments and variations may be made in the above-described invention without departing from the spirit of the invention wherein apparatus and methods have been provided for generating a first motion picture as an illumination receiver or support table or both move along a relative movement path, and thereafter generating a second motion picture by automatically causing the illumination receiver or support table or both to follow the me relative movement path as that selected originally by the operator. The first motion picture and second motion picture are thereafter subtracted on a frame-by-frame basis after suitable alignment and registration to obtain a subtracted motion picture of a subject whereby background information common to both is eliminated and only the differences appear.

APPENDIX A

```
**** TSO FOREGROUND HARDCOPY ****
DSNAME=HSE412.MIDAS.FORT                                (LANDMARK)

C MIDAS(LANDMARK)
      REAL Y(25),D(7,15,15)/1125*0./,VAR(3),VARMIN(3),SP(2)
      INTEGER*2 U/0/
C     INTEGER*2 U/0/,PU(54,54)
      LOGICAL *1 S(470,92),P(432,54),T(2)
      EQUIVALENCE(T(1),U)
      DO 5 K = 1, 110
5     READ(18,6,END=99) SLUFF
      DO 15 KV = 1, 92
15    READ(18,6,END=99) (S(L,KV),L=1,470)
      DO 9 KV = 1, 54
9     READ(17,2,END=99) (P(L,KV),L=1,432)
      DO 1 NV = 1, 15
      IF(NV.EQ.1) GO TO 22
      DO 33 KV = 28, 92
      DO 33 L = 1, 470
33    S(L,KV-27) = S(L,KV)
      DO 34 KV = 66, 92
34    READ(18,6,END=99) (S(L,KV),L=1,470)
6     FORMAT(14X,19A1,108(4A1),19A1)
      DO 10 KV = 28, 54
      DO 10 L = 1, 432
10    P(L,KV-27) = P(L,KV)
      DO 3 KV = 28, 54
3     READ(17,2,END=99) (P(L,KV),L=1,432)
2     FORMAT(108(4A1))
22    DO 1 NH = 1, 15
      MV = 19
      NVB = MV
      MH = (NH-1) * 27 + 19
      NHB = MH
C     NBASE = (NH-1)*27
C     DO 21 K = 1, 54
C     DO 21 L = 1, 54
C     T(2) = P(NBASE+L,K)
C21   PU(L,K) = U
      MU = 8
      MUP = 8
      DO 18 NOP = 1, 8
      VARMIN(3) = 1.E50
      KY = 0
      DO 4 JV = 1, 5
      IV = JV - 3
      DO 4 JH = 1, 5
      IH = JH - 3
      KY = KY + 1
      LV = MV + IV * MU
      LH = MH + IH * MU
      CALL ZERO
      DO 7 KV = 1, 54, MU
      DO 7 KH = 1, 54, MU
      KLV = LV + KV
      KLH = LH + KH
      IF(KLV.LT.1.OR.KLV.GT.92.OR.KLH.LT.1.OR.KLH.GT.470) GO TO 8
      T(2) = S(KLH,KLV)
      SP(1) = U
      T(2) = P((NH-1)*27+KH,KV)
      SP(2) = U
C     SP(2) = PU(KH,KV)
```

```
              GO TO 14
8           SP(1) = 0.
            SP(2) = 255.
14        CALL CUM(SP)
7         CONTINUE
          CALL STATS(RATIO,VAR)
            DISTSQ = (NVB-LV)**2+(NHB-LH)**2
            VAR(3) = VAR(3) * ( 1. + DISTSQ / 1000. )
            Y(KY) = VAR(3)
          IF(VAR(3).GT.VARMIN(3)) GO TO 4
            DISTSM = DISTSQ
            LVMIN = LV
            IHMIN = IH
            LHMIN = LH
            RMIN = RATIO
          DO 25 L = 1, 3
25          VARMIN(L) = VAR(L)
4         CONTINUE
            LDVMIN = NVB - LVMIN
            LDHMIN = NHB - LHMIN
          IF((NV-1)/4*4.EQ.NV-1.AND.(NH-1)/4*4.EQ.NH-1)
         &PRINT 23, NV,NH,NVB,NHB,MV,MH,LDVMIN,LDHMIN,MU,NOP,
         & IVMIN,IHMIN,LVMIN,LHMIN,RMIN,VARMIN,DISTSM
23          FORMAT(7(2I4,2X),5F12.3)
          IF((NV-1)/4*4.EQ.NV-1.AND.(NH-1)/4*4.EQ.NH-1) PRINT 19, Y
19          FORMAT(5F8.1)
            MV = LVMIN
            MH = LHMIN
            MUPP = MUP
            MUP = MU
            MU = IVMIN**2 + IHMIN**2
            MU = (MU+MU+MUP) / 3
          IF(MU.LT.1) MU = 1
          IF(MUPP+MUP+MU.LE.6) GO TO 17
18        CONTINUE
17          D(1,NH,NV) =        (NV-1)*27 + 19 + 27.5
            D(2,NH,NV) =        (NH-1)*27 + 19 + 27.5
            D(3,NH,NV) = NVB - LVMIN
            D(4,NH,NV) = NHB - LHMIN
          DO 26 L = 1, 4
26          D(L+4,NH,NV) = VARMIN(L)
          PRINT 23, NV,NH,NVB,NHB,MV,MH,LDVMIN,LDHMIN,MU,NOP,
         & IVMIN,IHMIN,LVMIN,LHMIN,RMIN,VARMIN,DISTSM
          PRINT 27, NV,NH,(D(L,NH,NV),L=1,7),RMIN
27          FORMAT(2I3,8F10.3)
1         CONTINUE
          WRITE(7,20) D
          PRINT 20, D
20          FORMAT(7F10.3)
99        STOP
          END
          SUBROUTINE CUM(SP)
C 1=SCOUT    2=CONTRAST    3=2-1 DIFF
          REAL SP(3),SX(3),SXX(3),VAR(3)
          SP(3) = SP(2) - SP(1)
          DO 1 L = 1, 3
            SX(L) = SX(L) + SP(L)
1           SXX(L) = SXX(L) + SP(L)**2
          PNO = PNO + 1.
          RETURN
          ENTRY ZERO
          DO 2 L = 1, 3
            SX(L) = 0.
```

```
2       SXX(L) = 0.
        PNO = 0.
      RETURN
      ENTRY STATS(RATIO,VAR)
      DO 3 L = 1, 3
3       VAR(L) = (SXX(L)-SX(L)**2/PNO)/(PNO-1.)
        RATIO = VAR(1) / VAR(3)
      RETURN
      END
```

APPENDIX B

```
**** TSO FOREGROUND HARDCOPY ****
DSNAME=HSE412.M.FORT                                 (TRANSFOR)

C M(TRANSFOR) TRANSFORMS S(72X72) INTO B(64X64) AND COMPARES WITH C
      REAL R(10,2)
      LOGICAL *1 T(2)
      INTEGER *2 S(72,72),C(54,54),B(54,54)
      EQUIVALENCE(T(1),U)
      READ(8,5,END=99) R
5     FORMAT(15X,F15.6)
      WRITE(6,5,END=99) R
      REAL MEAN(3),VAR(3),SC(3)
      DO 1 NV = 1, 15
      DO 1 NH = 1, 15
        READ(22,2,END=99) S
2       FORMAT(72I3)
        READ(23,3,END=99) C
3       FORMAT(54I3)
      CALL ZERO
      DO 4 KV = 1, 54
        V = ((NV-1)*27+KV)/216.5 - 1.
      DO 4 KH = 1, 54
        H = ((NH-1)*27+KH)/216.5 - 1.
      ZVD=R(1,1)+R(2,1)*V+R(3,1)*H+R(4,1)*V*V+R(5,1)*V*H+R(6,1)*H*H
     &+R(7,1)*V*V*V+R(8,1)*V*V*H+R(9,1)*V*H*H+R(10,1)*H*H*H
      ZHD=R(1,2)+R(2,2)*V+R(3,2)*H+R(4,2)*V*V+R(5,2)*V*H+R(6,2)*H*H
     &+R(7,2)*V*V*V+R(8,2)*V*V*H+R(9,2)*V*H*H+R(10,2)*H*H*H
        ZVA = 9 + KV - ZVD
        ZHA = 9 + KH - ZHD
        IV = ZVA
        IH = ZHA
        ZV = ZVA - IV
        ZH = ZHA - IH
       SC(1) = S(IH,IV)*(1.-ZH)*(1.-ZV) + S(IH+1,IV)*ZH*(1-ZV)
     &       + S(IH,IV+1)*(1.-ZH)*ZV + S(IH+1,IV+1)*ZH*ZV + .5
        B(KH,KV) = SC(1)
        SC(2) = C(KH,KV)
      CALL CUM(SC)
      IF(KV.NE.27.OR.KH.NE.27) GO TO 4
        ZVDM = ZVD
        ZHDM = ZHD
4     CONTINUE
      CALL STATS(MEAN,VAR,PNO,RATIO)
      PRINT 23, NV,NH,ZVDM,ZHDM,MEAN,VAR,RATIO
      WRITE(7,23) NV,NH,ZVDM,ZHDM,MEAN,VAR,RATIO
23    FORMAT(2I3,2F4.1,7F8.3)
      IF(NV/2*2.EQ.NV.OR.NH/2*2.EQ.NH) GO TO 86
        WRITE(24,3) B
86    IF(NV.NE.1.AND.NV.NE.8.AND.NV.NE.15) GO TO 1
      IF(NH.NE.1.AND.NH.NE.8.AND.NH.NE.15) GO TO 1
      DO 88 KV = 3,72,3
88      PRINT 87,KV,(S(L,KV),L=3,72,3)
```

```
  87      FORMAT(33I4)
          PRINT 87
          DO 89 KV = 3,54,3
  89      PRINT 87,KV,(C(L,KV),L=3,54,3)
          PRINT 87
          DO 79 KV = 3,54,3
  79      PRINT 87,KV,(B(L,KV),L=3,54,3)
  1       CONTINUE
  99      STOP
          END
          SUBROUTINE CUM(SC)
C  1=SCOUT    2=CONTRAST    3=2-1 DIFF
          REAL MEAN(3),SC(3),SX(3),SXX(3),VAR(3)
          SC(3) = SC(2) - SC(1)
          DO 1 L = 1, 3
          SX(L) = SX(L) + SC(L)
  1       SXX(L) = SXX(L) + SC(L)**2
  19      FORMAT(10F8.1)
          PNO = PNO + 1.
          RETURN
          ENTRY ZERO
          DO 2 L = 1, 3
          SX(L) = 0.
  2       SXX(L) = 0.
          PNO = 0.
          RETURN
          ENTRY STATS(MEAN,VAR,PNOX,RATIO)
          DO 3 L = 1, 3
          MEAN(L) = SX(L)/PNO
  3       VAR(L) = (SXX(L)-SX(L)**2/PNO)/(PNO-1.)
          RATIO = VAR(1) / VAR(3)
          PNOX = PNO
          RETURN
          END
**** TSO FOREGROUND HARDCOPY ****
DSNAME=HSE412.M.FORT                              (P1R      )

/PROB TITLE='M(P1R) WINDOW TRANSFORMATION FOR MAPPING  SEPT80'.
/INP VAR=11,CASES=225,UNIT=7,FORMAT='(2F3.0,2F4.0,7F8.3)'.
/VAR NAME=VERT,HORZ,DVER,DHOR,MEANS,MEANC,MEAND,VARS,VARC,VARD,RATIO,
 DIST,WT,V,H,V2,VH,H2,V3,V2H,VH2,H3,WEIGHT.WEIGHT=WEIGHT.
 ADD=12.
/TRAN X(14)=(X(1)*27.+.5)/216.5-1..
      X(15)=(X(2)*27.+.5)/216.5-1..
 DIST=((X(3)-0.)**2+(X(4)-3.)**2).
 WT=RATIO/MEAND*4./(4.+DIST).
X(16) = X(14)*X(14).
X(17) = X(15)*X(14).
X(18) = X(15)*X(15).
X(19) = X(14)*X(14)*X(14).
X(20) = X(15)*X(14)*X(14).
X(21) = X(15)*X(15)*X(14).
X(22) = X(15)*X(15)*X(15).
WEIGHT=WT.
/REGR DEPEND=3,INDEP=14 TO 22./END
/REGR DEPEND=4,INDEP=14 TO 22./END
```

APPENDIX C

```
**** TSO FOREGROUND HARDCOPY ****
DSNAME=HSE412.M.FORT                              (SUBTRACX)

C M(SUBTRACX) NON-LIN SUBTRACTION OF ADJUSTED SCOUT FROM CONTRAST FILM
      LOGICAL *1 TC(2),C(432)
```

```
          INTEGER *2 UC/0/,B(432,54)
          EQUIVALENCE(TC(1),UC)
C TABLE OF DENSITY X EXPOSURE AND INVERSE TABLE
          REAL DI(256,2),TAB(2)/0.,.5/
          INTEGER *2 ID(776),I/1/
          DO 11 IT = 1,2
          DO 11 N = 1,256
            D = ((N-1+TAB(IT)) - 128.) / 128.
11        DI(N,IT)=.33309+.18896*D+.05505*D**2+.02468*D**3
         C+.10142*D**6+.17668*D**15-.09570*D**16
          PRINT 15,DI
15        FORMAT(2(2X,5F8.4))
          DO 12 K = 1,776
            Y = (K-1) * .001
          DO 14 N = 1,256
          IF(Y.GT.DI(N,2)) GO TO 14
            ID(K) = N - 1
          GO TO 12
14        CONTINUE
12        I = N
          PRINT 16,ID
16        FORMAT(2(2X,5I4))
          DO 1 NV = 1,8
          DO 4 IB = 1,8
            IZ = IB * 54
            IA = IZ - 53
          DO 4 KV = 1, 54
4           READ(24,3) (B(L,KV),L=IA,IZ)
3         FORMAT(54I3)
          DO 1 KV = 1, 54
            READ(28,5,END=99) C
          DO 2 NH = 1, 432
            TC(2) = C(NH)
            NC = UC + 1
            NB = B(NH,KV) + 1
          IF(NC.GT.256) NC = 256
          IF(NB.GT.256) NB = 256
            IY = (DI(NC,1)-DI(NB,1)+.16) * 1000. + 1.
          IF(IY.LT.1) IY = 1
          IF(IY.GT.776) IY = 776
            UC = ID(IY)
          IF(UC.LT.0) UC = 0
          IF(UC.GT.255) UC = 255
2         C(NH) = TC(2)
1         WRITE(31,5) C
5         FORMAT(108(4A1))
99        STOP
          END
```

What is claimed is:

1. An image acquisition system for generating a subtracted image motion picture of a selected feature of a biological subject comprising:

imaging means including an illumination source, a support for the subject and an illumination receiver, for generating an image of the selected subject feature, at least one of the illumination source, the support and the illumination receiver being movable by an operator whereby there is relative movement between the subject and the illumination receiver along an imaging path selected by the operator;

means for causing at least one of the illumination source, support and illumination receiver to move so that the relative movement between the subject and the illumination receiver is along the imaging path to duplicate said imaging path;

means for generating and storing a sequence of first frames of the image to define a first motion picture as the operator causes relative movement between the subject and the illumination receiver to define the imaging path and a sequence of second frames of the image to define a second motion picture as the relative movement between the subject and the illuminating receiver along the imaging path is duplicated;

means for aligning and registering the first motion picture and the second motion picture on a frame-by-frame basis; and means for subtracting the aligned second motion picture from the first motion picture on a frame-by-frame basis for generating a subtracted image motion picture of the subject as the relative movement between the illumination receiver and the subject occurs along the imaging path.

2. The system of claim 1 wherein the illumination source is an X-ray generator and the illumination receiver is sensitive to X-ray energy.

3. The system of claim 1 wherein the illumination source is an ultrasound generator and the illumination receiver is sensitive to ultrasound energy.

4. The system of claim 1 further comprising means for maintaining a constant illumination source exposure level during the generation of the first motion picture and the generation of the second motion picture.

5. The system of claim 1 wherein the first motion picture is generated photographically, the second motion picture is generated photographically, and the means for subtracting comprises apparatus for performing frame-by-frame photographic subtraction.

6. The system of claim 1 wherein the support for the subject is stationary and the illumination receiver is movable to define the relative movement along the imaging path.

7. The system of claim 1 wherein the illumination receiver is stationary and the support for the subject is movable to define the relative movement along the imaging path.

8. The system of claim 1 wherein each first frame and each second frame is digitized to define a plurality of first frame pixels for each first frame and a plurality of second frame pixels for each second frame, each first frame pixel and each second frame pixel defined by an address specifying its position in the frame and an illumination energy density value for defining the density of the illuminating energy impinging on the pixel, the means for generating and storing further comprising:

memory means for storing the illuminating energy density values of each pixel; and the subtracting means further comprising:

means for repeatedly selecting a first frame generated at a selected position along the imaging path and a corresponding second frame generated at substantially the same position along the imaging path, and, pixel differencing means for subtracting the pixel illumination energy density value of each pixel in the selected second motion picture frame from the pixel illumination energy density value of the pixel in the selected first motion picture frame having a corresponding pixel address.

9. The system of claims 1 or 5 and 8 wherein the means for generating a sequence of first frames and second frames further comprises:

means for generating a sequence of unprocessed first frames;

means for registering at least two of the unprocessed first frames; and means for averaging the registered unprocessed first frames to define each first frame.

10. The system of claim 1 or 5 or 8 wherein the means for generating a sequence of first frames and second frames further comprises:

means for generating a sequence of unprocessed second frames;

means for registering at least two of the unprocessed second frames; and means for averaging the registered unprocessed second frames to define each second frame.

11. The system of claim 9 wherein the means for generating a sequence of first frames and second frames further comprises:

means for generating a sequence of unprocessed second frames;

means for registering at least two of the unprocessed second frames; and means for averaging the registered unprocessed second frames to define each second frame.

12. An image acquisition system for generating a subtracted variable density motion picture of a biological subject wherein there is relative movement of the subject while the motion picture is being taken, comprising:

a source of illuminating energy for illuminating the subject;

means for receiving the illuminating energy and generating a variable density image;

a support for positioning the subject between the source of illuminating energy and the receiving means;

means for selectively changing the relative position between the support and the means for receiving for defining a first relative movement path;

position sensing means for sensing the relative position between the support and the receiving means for generating sensed position signals representative of the relative position between the subject and the receiving means along the first relative movement path;

means for storing the sensed position signals;

means for generating position control signals from the stored position signals;

means for subsequently driving at least a selected one of the support and the receiving means to vary the relative position between the support and the receiving means in response to the position control signals for defining a second relative movement path substantially duplicative of the first relative movement path;

means for generating a first motion picture of the variable density image of the subject during the relative movement along the first relative movement path, and generating a second motion picture of the variable density image of the subject during the relative movement along the second relative movement path wherein the first motion picture has a plurality of first frames, each first frame defining a picture at a specific geometric position along the first relative movement path and the second motion picture has a plurality of second frames, each second frame defining a picture at a specific geometric position along the second relative movement path;

means for aligning the first frames in the first motion picture and the second frames in the second motion picture whereby each first frame and second frame which is aligned represent variable density images at substantially corresponding geometric positions relative to the subject along the respective first and second relative movement paths; and means for subtracting each second frame from each corresponding aligned first frame for defining a plurality of subtracted variable density frames to define the subtracted variable density motion picture.

13. The system of claim 12 wherein the source of illuminating energy is an X-ray generator and the receiving means is sensitive to X-ray energy.

14. An image acquisition system for generating a subtracted image motion picture of a biological subject comprising:
   imaging means for periodically generating a motion picture frame wherein the received illumination at a plurality of predefined locations in the frame is sensed and digitized, to define an array of digitized pixel densities, the array defining a digitized motion picture frame;
   means for selectively moving the imaging means along an imaging path whereby there is relative movement between the subject and the imaging means;
   means for periodically generating digitized position information representative of the position of the imaging means relative to the subject;
   means for storing the digitized position information;
   means for subsequently automatically moving the imaging means in response to the stored digitized position information for substantially retracing the relative movement between the subject and the imaging means along the imaging path whereby a first sequence of digitized first frames is generated during the selective movement along the imaging path and a second sequence of digitized second frames is generated during the subsequent retrace along the imaging path;
   means for storing the first sequence of digitized first frames and the second sequence of digitized second frame;
   means for sampling the digitized position information after each digitized first frame and digitized second frame is generated and storing the sampled digitized position information with each digitized picture frame and each digitized second frame respectively for indicating the position along the imaging path whereat each first frame and each second frame was generated; and
   means for aligning the first frames with the second frames in accordance with the correspondence between the sampled digitized position information stored and associated with each first frame and second frame.

15. The system of claim 14 wherein the imaging means is an X-ray imaging device.

16. The system of claim 14 wherein the imaging means is an ultrasound imaging device.

17. A method for generating a subtracted image motion picture of a selected feature of a biological subject comprising the steps of:
   generating an image of the selected subject feature, using an imaging device including an illuminating source, a support for the subject and an illumination receiver, as at least one of the illuminating source, the support and the illumination receiver is moved by an operator whereby there is relative movement between the subject and the illumination receiver along an imaging path;
   causing at least one of the illuminating source, support and illumination receiver to move so that the relative movement between the subject and the illumination receiver is along the imaging path to duplicate said imaging path;
   generating and storing a sequence of first frames of the image to define a first motion picture as the operator causes relative movement between the subject and the illumination receiver to define the imaging path and a sequence of second frames of the image to define a second motion picture as the relative movement between the subject and the illuminating receiver along the imaging path is duplicated;
   aligning and registering the first motion picture and the second motion picture on a frame-by-frame basis; and
   subtracting the aligned second motion picture from the first motion picture on a frame-by-frame basis for generating a subtracted image motion picture of the subject as the relative movement between the illumination receiver and the subject occurs along the imaging path.

18. The method of claim 17 further comprising the step of maintaining a constant illuminating source exposure level during the generation of the first motion picture and the generation of the second motion picture.

19. The method of claim 17 wherein the first motion picture is generated photographically, the second motion picture is generated photographically, and the step of subtracting comprises frame-by-frame photographic subtraction.

20. The method of claim 17 wherein the step of generating an image comprises the further steps of keeping the support for the subject stationary and moving the illumination receiver to define the relative movement along the imaging path.

21. The system of claim 17 wherein the step of generating an image comprises the further steps of keeping the illumination receiver stationary and moving the support table for the subject to define the relative movement along the imaging path.

22. The method of claim 17 comprising the further steps of digitizing each first motion picture frame and each second motion picture frame to define a plurality of first frame pixels for each first frame and a plurality of second frame pixels for each second frame, each first frame pixel and each second frame pixel defined by an address specifying its position in the frame and a light density value for defining the density of the illuminating energy from the illumination source impinging on the pixel, step of generating and storing further comprising the steps of:
   storing the illuminating energy density values of each pixel; and the step of subtracting further comprising:
   repeatedly selecting a first frame generated at a selected position along the imaging path and a corresponding second frame generated at substantially the same position along the imaging path; and
   subtracting the pixel illumination energy density value of each pixel in the selected second motion picture frame from the pixel illumination energy density value of the pixel in the selected second motion picture frame having a corresponding pixel address.

23. The method of claim 17 or 19 or 21 wherein the step of generating a sequence of first frames and second frames further comprises:
   generating a sequence of unprocessed first frames;
   registering at least two of the unprocessed first frames; and averaging the registered unprocessed first frames to define each first frame.

24. The method of claim 17 or 19 or 21 wherein the step of generating a sequence of first frames and second frames further comprises:
generating a sequence of unprocessed second frames;
registering at least two of the unprocessed second frames; and
means for averaging the registered unprocessed second frames to define each second frame.

25. The method of claim 23 wherein the step of generating a sequence of first frames and second frames further comprises:
generating a sequence of unprocessed second frames;
registering at least two of the unprocessed second frames; and
means for averaging the registered unprocessed second frames to define each second frame.

26. The method of claim 17 in which the subject is a biological vessel capable of accepting the injection of a contrast medium the method comprising the further steps of:
injecting a contrast medium material into the subject immediately prior to generating the first motion picture whereby the first motion picture is a motion picture of the contrast medium as it flows through the subject; and
generating the second motion picture after the contrast medium is dissipated from the subject whereby the second motion picture is taken when there is substantially no detectible contrast medium in the subject.

27. The method of claim 17 wherein the step of generating and storing the second motion picture generated occurs an extended length of time after performing the step of generating and storing the first motion picture whereby the resultant subtracted image motion picture shows only image differences which have occurred during the extended length of time.

28. The method of claim 27 comprising the further steps of injecting a contrast medium into the subject immediately before generating both the first motion picture and the second motion picture.

29. The method of claim 17 wherein the illumination source is an X-ray generator so that the first and second motion pictures are generated by X-rays interacting with the selected feature of the subject.

30. The method of claim 17 wherein the illumination source is an ultrasonic wave generator so that the first and second motion pictures are generated from ultrasonic waves interacting with the selected feature of the subject.

31. An image acquisition system for generating a subtracted image motion picture of a selected feature of a subject comprising:
imaging means including an illumination source, a support for the subject and an illumination receiver, for generating an image of the selected subject feature, at least one of the illumination source, the support and the illumination receiver being movable by an operator whereby there is relative movement between the subject and the illumination receiver along an imaging path selected by the operator;
means for causing the at least one of the illumination source, support and illumination receiver to move so that the relative movement between the subject and the illumination receiver is along the imaging path to duplicate said imaging path;
means for generating and storing a sequence of first frames of the image to define a first motion picture as the operator causes relative movement between the subject and the illumination receiver to define the imaging path and a sequence of second frames of the image to define a second motion picture as the relative movement between the subject and the illuminating receiver along the imaging path is duplicated;
means for aligning and registering the first motion picture and the second motion picture on a frame-by-frame basis; and
means for subtracting the aligned second motion picture from the first motion picture on a frame-by-frame basis for generating a subtracted image motion picture of the subject as the relative movement between the illumination receiver and the subject occurs along the imaging path.

* * * * *

UNITED STATES PATENT AND TRADEMARK OFFICE
CERTIFICATE OF CORRECTION

PATENT NO. : 4,448,200
DATED : May 15, 1984
INVENTOR(S) : Brooks et al

It is certified that error appears in the above-identified patent and that said Letters Patent are hereby corrected as shown below:

Column 1, line 12, "substrated" should be --subtracted--.

Column 3, line 38, "infra" should be --intra--.

Column 6, line 59, "translation" should be --translational--.

Column 7, line 16, "motorswhich" should be --motors which--.

Column 9, line 2, "exaclty" should be --exactly--.

Column 9, line 18, "retaces" should be --retraces--.

Column 9, line 64, "substraction" should be --subtraction--.

Column 11, line 30, delete "wherein".

Column 12, line 68, "10" should be --110--.

UNITED STATES PATENT AND TRADEMARK OFFICE
CERTIFICATE OF CORRECTION

PATENT NO. : 4,448,200   Page 2 of 2
DATED : May 15, 1984
INVENTOR(S) : Brooks et al It is certified that error appears in the above-identified patent and that said Letters Patent are hereby corrected as shown below:

Column 27, line 36, "frame" should be --frames--.

Signed and Sealed this

Fifth Day of March 1985

[SEAL]

Attest:

DONALD J. QUIGG

Attesting Officer        Acting Commissioner of Patents and Trademarks